United States Patent [19]

Kaufman

[11] 4,092,985
[45] June 6, 1978

[54] BODY ELECTRODE FOR ELECTRO-MEDICAL USE

[76] Inventor: John George Kaufman, 858 Condor Drive, Burlington, Ontario, Canada

[21] Appl. No.: 710,535

[22] Filed: Aug. 2, 1976

Related U.S. Application Data

[63] Continuation-in-part of Ser. No. 526,681, Nov. 25, 1974, Pat. No. 3,972,329.

[51] Int. Cl.² ............................................. A61N 3/06
[52] U.S. Cl. ................................ 128/303.13; 128/417
[58] Field of Search .......... 128/2.06 E, 2.1 B, 303.13, 128/404, 410, 411, 416, 417, 418, DIG. 4

[56] References Cited

U.S. PATENT DOCUMENTS

| | | | |
|---|---|---|---|
| 1,212,541 | 1/1917 | Morse | 128/417 X |
| 2,555,037 | 5/1951 | Jensen | 128/417 |
| 2,887,112 | 5/1959 | Smith | 128/417 |
| 2,943,627 | 7/1960 | Howell | 128/416 |
| 3,487,827 | 1/1970 | Edmark | 128/2.06 E |
| 3,542,010 | 11/1970 | Love | 128/2.1 E |
| 3,746,004 | 7/1973 | Jankelson | 128/410 |
| 3,817,252 | 6/1974 | Maurer | 128/416 |
| 3,828,766 | 8/1974 | Krasnow | 128/2.1 E |
| 3,848,600 | 11/1974 | Patrick, Jr. et al. | 128/417 |
| 3,993,049 | 11/1976 | Kater | 128/2.06 E |
| 3,998,215 | 12/1976 | Anderson et al. | 128/2.06 E |

FOREIGN PATENT DOCUMENTS

| | | | |
|---|---|---|---|
| 675,494 | 12/1963 | Canada | 128/417 |

*Primary Examiner*—Robert W. Michell
*Assistant Examiner*—Lee S. Cohen
*Attorney, Agent, or Firm*—Hiron & Rogers

[57] ABSTRACT

A body electrode for use as the indifferent, return electrode in electrosurgical and the like procedures includes a layer of fibrous webbing contacting a conductive metal plate of the electrode on one side and the patent's body on the other side. The layer of webbing is adapted to be wetted with aqueous conductive fluid medium applied thereto immediately prior to application of the electrode to the body. The webbing is of non-absorbent thermoplastic fibres, e.g. polyester, which will restrain the flow of but not substantially absorb the conductive fluid. The webbing layer is of 1/50 − ⅛ inch thickness and comprises non-absorbent fibres interwoven together in an interlocking manner.

8 Claims, 3 Drawing Figures

BODY ELECTRODE FOR ELECTRO-MEDICAL USE

CROSS REFERENCE TO RELATED APPLICATIONS

This application is a continuation-in-part of my United States patent application Ser. No. 526,681, filed Nov. 25, 1974 entitled, "Body Electrode for Electro-Medical Use", issued Aug. 3, 1976 as U.S. Pat. No. 3,972,329.

FIELD OF THE INVENTION

This invention relates to body electrodes for use in electrosurgical and electromedical procedures, of the type which are placed in contact with the body to act as the return electrode during such procedures. More specifically, the invention relates to such a body electrode including a layer of textile or webbing material to be placed in contact with the patient's skin as part of the return electrode, of specific form.

BACKGROUND OF THE INVENTION

It is known to provide body electrodes for electro-medical use comprising a conductive metal plate having a terminal by means of which it can be electrically connected to the electro-surgical unit, and a layer of fibrous material wetted or impregnated with a liquid or semi-solid conductive medium, the inner surface of which is adapted to contact the patient's skin and the outer surface of which contacts the surface of the metal plate. It is very important, in electro-surgical procedures, that the body electrode contact the patient's skin in electrically conductive manner over a substantial area, so as to distribute the electric current over a sufficiently large area to eliminate excessive heating effects.

It is also important to avoid direct contacts of the metal plate and the patient's skin, since this is likely to cause burning of the patient's skin. The electrical conductivity achieved between a conductive metal plate and a patient's skin is too low to permit passage of electric currents of the magnitude used in electro-surgical techniques therebetween without serious resistive heating effects, resulting in burns to the patient's skin. Very high frequency, high voltage alternating electric currents are used in electro-surgical techniques. The provision of a conductive medium, such as a conductive gel, liquid, cream or paste, between the metal plate and the patient's skin, is thus very important. The conductive medium is generally water based, and contains electrolytes, and has the ability to penetrate the skin to some extent to provide an electrically conductive path from the patient's body to the metal plate, of low electrical resistance. The skin is a generally non-conductive, dielectric material, and by penetrating the skin the conductive medium provides an electrically conductive path through the skin.

It will thus be appreciated that the conductive medium has an important role to play in the satisfactory performance of any return body electrode. If the electrode is to perform satisfactorily, not only must the conductive medium be of high electrical conductivity and be able to penetrate the patient's skin to the correct degree to provide the low electrical resistive return path to the metal plate, but also the conductive medium must be held in the right location relative to the metal plate. It must extend over the whole area of the metal plate, so that the electric current is distributed over the whole area. It must be held so that, during use, it does not run out or become squeezed out from between the metal plate and the skin when the electrode is tightly affixed to the body, even when the electrode is disposed vertically. It must not dry out prior to or during use, after application to the electrode, so as to reduce its electrical conductivity. Moreover, it should provide a thin conductive layer of essentially uniform thickness between the metal plate and the skin, for best distribution of current over the area of the electrode.

BRIEF DESCRIPTION OF THE PRIOR ART

It has been proposed in the past to provide body electrodes comprising a metal plate, to the underside of which a suitable conductive medium is applied. Without some means for holding the conductive medium in place, however, there is a severe risk that the medium will run or be squeezed from between the plate and the skin, with consequent direct metal-skin contact. Such an arrangement is not satisfactory for electro-surgical procedures, involving currents of large magnitude.

A commoner expedient is to use an absorbent pad of some sort, soaked with the conductive medium, between the metal plate and the skin, the pad normally being attached to the metal plate by suitable means. For example, U.S. Pat. No. 3,828,766 Krasnow proposes use of a lower gel pad of open cell material such as foam polyurethane. U.S. Pat. No. 3,817,252 Maurer similarly discloses the use of a skin interface pad of foam material or cloth. Canadian Pat. No. 675,494 Gilman discloses an inner pad of absorbent felt or fabric material. U.S. Pat. No. 3,848,600 Patrick et al discloses a body-contacting pad of a sponge-like cellular matrix (e.g. polyurethane foam or other like absorbent material), and as an alternative nonwoven cotton fabric discs, saturated with electrolyte.

The prior art proposals have, however, been found to exhibit one or more disadvantages. The use of cellular foam materials such as foam polyurethanes as the pad to hold the conductive medium entails the use of relatively thick pads, in order to ensure that there is no direct skin-metal contact therethrough. The body electrode must in practice be tightly secured to the body, which means that the cellular pad will be under compression. If a thin cellular pad is used, thinner than about ¼ inch, then in effect there may be direct contact between metal and skin when the pad is compressed on application, or at least local areas of contact where there is no intervening conductive medium as a result of such compression. In practice, cellular foam pads of thickness of about ½ inch are used. The use of pads of such thickness raises additional problems. Firstly, the amount of conductive medium required to saturate such a thick pad to provide the necessary conductive path over a large area is excessive. Secondly, with such a thick, compressable pad, the thickness of the conductive medium soaked pad will in practice vary from location to location across the area of the electrode, i.e., the distance from the metal plates to the body varies from place to place. This detracts from the ability of the electrode to distribute the current evenly over the surface of the electrode. The foam-conductive medium itself presents some electrical resistance, so that the current flow becomes uneven due to this variation in thickness, and may lead to local overheating. Thirdly, since the conductive medium itself offers a degree of electrical resistance, it is desirable to keep the thickness of the layer of conductive medium as small as possible consistent with the prevention of local metal-skin contacts, to minimize the risk of general resistance heating.

The use of absorbent textile or felted fibrous pads overcomes some of the above problems, but presents others. The conductive media employed in this application are water based. Hydrophilic absorbent fibres such as cotton absorb at least the aqueous portion of the conductive medium and cause the medium to dry out and lose a portion of its conductivity, and hinder its penetration of the patient's skin to provide a readily conductive path therethrough. Also, an absorbent textile pad saturated with aqueous conductive medium presents, in effect, a discontinuous electrically-conductive phase due to the absorbence of the medium by the fibres, and hence increased electrical resistance. Further, saturated absorbent fibres such as cotton fibres have very little mechanical strength, and are liable to tear in use, with the attendant risk of establishing direct skin-metal contact. There is thus a tendency to use extra thick absorbent textile pads of this nature, to minimize this risk.

One factor in the choice of the above types of conductive medium holding pads previously has been the desire to provide pre-gelled pads and electrodes, i.e., electrodes having lower body-contacting pads to which the conductive medium is pre-applied, e.g. on manufacture. In such case, whilst the medical practitioner does not have to apply the medium immediately prior to use, the problem arises that the pad and medium must be designed to prevent drying out or running off of the medium during transit or storage of the electrode, in a variety of positions. Such problems have lead to the adoption of conductive media of relatively high viscosity, and thereby lacking in skin penetration, and pads of a highly absorbent nature.

SUMMARY OF THE PRESENT INVENTION

An object of the present invention is to provide an improved body electrode for electro-surgical use. A more specific object of the invention is to provide a body electrode of the disposable type having associated therewith an inproved conductive medium holding means for contacting the patient's body.

According to the present invention, there is provided a body electrode for electro-medical use, comprising:

a cover sheet member having an inner surface for facing towards the body and an outer surface for facing away therefrom;

a flexible, electrically conductive metal sheet member having an outer surface presented towards the inner surface of said cover sheet member, an inner surface for facing towards the body;

terminal means in electrically conductive relation to said metal sheet member;

means for attaching the body electrode to a patient's body;

a layer of water permeable woven fibrous webbing covering in its entirety the inner surface of said metal sheet member and adapted to receive and restrain the flow of electro conductive medium of thin semi-solid or fluid consistency applied thereto, said layer having a thickness of from about 1/50 to about ⅛ inch, the fibres of said webbing being of low water absorbency and being interwoven together into said webbing in interlocking fashion.

By "fibres of low water absorbency" is meant fibres which, on immersion in water under room temperature and pressure conditions, will absorb not more than about 5% of their own weight of water, discounting water clinging to the fibre surface and which can be removed by a simple shake. By "fibres interwoven together in interlocking fashion" is meant any type of weave, knit or other conjunction of fibres whereby, if one fibre becomes ruptured at any single location, that fibre remains tightly bound to the webbing and cannot simply be pulled out, as a consequence of each single rupture.

DESCRIPTION OF THE PREFERRED EMBODIMENTS

The body electrode according to the present invention is preferably a disposable electrode, the cover sheet member of which is elastically, resiliently stretchable, and is affixed to the conductive metal sheet member near one end thereof, the remaining, major area portion of the conductive sheet member extending to the other end thereof remaining unsecured to the cover sheet member and thereby adapted to permit relative free movement between the cover sheet member and the conductive metal sheet member. The means for attaching the body electrode to the patient's body comprises two separate and distinct adhesive sections in fixed relation to the cover sheet member, adjacent either end thereof, so that the electrode as a whole can be applied to the patient's body with the cover sheet member in a stretched condition. In such arrangement, the resilient retractive force of the cover sheet urges the webbing layer into close contact with the patient's skin. It is however preferred in such an arrangement that the webbing be of elastically stretchable fibres, such that the webbing be capable of resilient stretching in both the longitudinal and transverse directions to an extent of at least 20%. In the preferred embodiment, the webbing is secured to the elastic cover sheet member over at least a portion of the periphery thereof, with the conductive metal plate sandwiched between the webbing and the cover sheet member and having a degree of free movement relative thereto. In this embodiment, therefore, the webbing is arranged to be resiliently stretchable as above, to accomodate the stretching of the cover sheet member.

A further desirable feature for the webbing according to the preferred embodiment of the invention is that it be of fibres which are ultrasound weldable to the material comprising the cover sheet. Essentially, ultrasound weldable fibres are thermoplastic synthetic fibres. To accomodate the stretching action of the cover sheet member described above, the webbing should be stretchably connected to the cover sheet member. Adhesive connection has been found unsatisfactory in practice since adhesives which are sufficiently effective in securing the components together are generally insufficiently elastic. Stitching the components together is inconvenient in large scale manufacture. It has been found that ultrasound spot welding is the most satisfactory means of stretchably connecting the webbing to the elastic cover sheet member (which is preferably of rubber or stretchable foam plastic), since this method is simple, efficient and can be carried out rapidly and economically on commercial scale production lines.

Specific examples of types of fibres from which the webbing for use in the present invention can be prepared include non-absorbent thermoplastic polyesters, non-absorbent thermoplastic polyamides, non-absorbent polyacrylonitriles, polyethylene and polypropylene.

Especially preferred are polyesters, for example in the form of interwoven polyester crepe fabric.

The body electrode of the preferred embodiment is intended for use in a non-pre-gelled manner, i.e., to have the fluid or semi-solid conductive medium applied to the webbing by the medical practitioner immediately prior to application of the electrode to the body. The form of webbing defined herein permits efficient and technically satisfactory use of the electrodes in this manner. The webbing will hold in place, without absorbing, aqueous conductive fluid media of very thin watery consistency, desirable for use on grounds of easy, thorough and rapid pentration of the patient's skin thereby. Conductive medium comprising in excess of 90% water can be used satisfactorily with electrodes according to the invention. The webbing nevertheless provides sufficient restraint substantially to prevent running and squeezing out of the medium from under the electrode after application even in a condition where the cover sheet is elastically stretched. Since the webbing does not absorb the conductive medium but merely holds it in position, a return electrical path of high conductivity and low resistance is provided to the metal plate. The webbing can be made extremely thin, and provides a layer of substantially uniform thickness over the area of the electrode.

DETAILED DESCRIPTION OF THE PREFERRED EMBODIMENT

Figure 1:
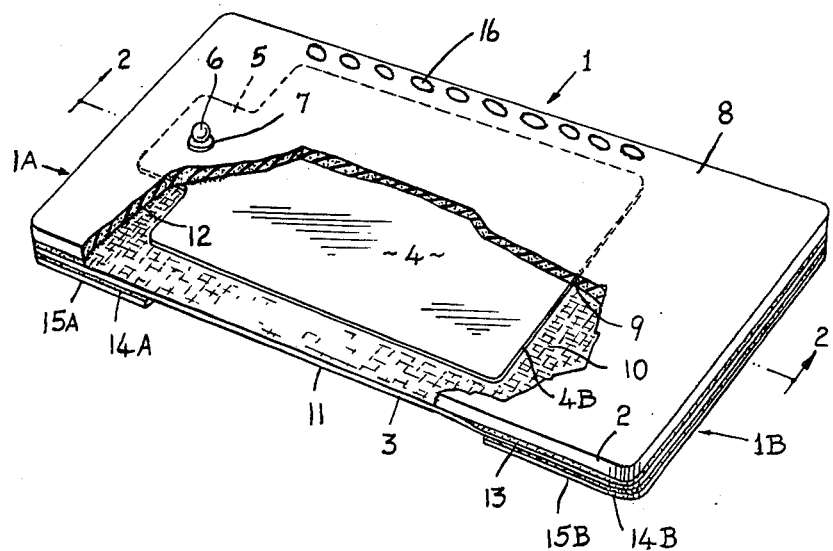
FIG. 1 is a view in perspective showing the outer side of a preferred embodiment of the novel electrode with a portion cut away to reveal the structure thereof.

In the drawings, wherein like reference characters indicate like parts, the reference number 1 indicates generally a body electrode constructed in accordance with one preferred embodiment of the invention. The terms "outer" and "inner" as used herein with regard to the constituent elements of the illustrated electrode relate to the position of the elements or their surfaces relative to the person's body or limb against which the electrode 1 is placed, in a direction generally transverse to the body or limb.

In the illustrated embodiment, electrode 1 generally comprises an elastically stretchable, electrically insulating, cover sheet member 2, a stretchable, porous inner layer of webbing 3, an elongated, flexible, electrically conductive metal sheet member 4, terminal means 6 adapted for electrical connection to a return cable (not shown), and adhesive means 14A, 14B.

As used herein in relation to cover sheet member 2, the term "elastically stretchable" describes its significant tendency to return to its original size, shape or position after being stretched, i.e., its resilience. It has been found that two suitable materials for use in fabricating cover sheet member 2 are rubber and closed-cell foam plastic, which are both capable of being stretched and sufficiently elastic for operation of the electrode as hereinafter described.

Webbing layer 3, in addition to being stretchable, is water permeable, porous and therefore capable of being wetted by an electrically conducting agent such as a conducting gel. This layer is described in more detail below.

Conductive sheet member 4 may be fabricated from a metallic sheet material such as copper, stainless steel or aluminum, which are all highly conductive and sufficiently flexible to conform to the gently convex contours of a limb or other portion of a person's body.

Figure 2:
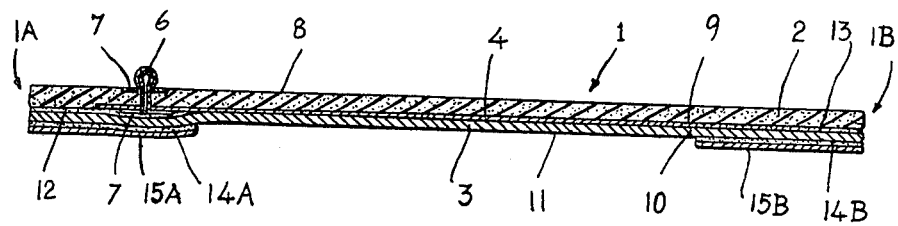
FIG. 2 is an enlarged view in section taken along the line 2—2 of FIG. 1.

As better illustrated in FIG. 2, conductive sheet member 4 is interposed between the cover sheet member 2 and webbing layer 3, which are all generally rectangular in shape. Conducting member 4 is smaller in size than both the outer member 2 and the webbing layer 3 (which are generally the same size. Thus, webbing layer 3 covers the entire inner surface of the conductive element 4. Conductive member 4 is positioned with its perimetric edge in inwardly spaced relation to the perimetric edge of cover sheet member 2 and of webbing layer 3.

The webbing layer 3 is secured to the cover sheet member 2 along both of its longitudinal edges by a series of spot ultrasound welds 16 (FIG. 1). The welds 16 are disposed outwardly of the perimeter of the metal conductive member or plate 4, so that the plate 4 is sandwiched between the webbing layer 3 and cover sheet member 4 but is unsecured to either of them over the major portion of its area.

As illustrated, the terminal means, in the form of a conventional male snap fastener 6 having crimped edges 7, is connected in electrically conducting relation to conductive sheet member 4 and fixedly secures the cover sheet member 4 in the vicinity of electrode end 1A.

The cover sheet member 2 has an outer surface 8 and an inner surface 9. Snap fastener 6 projects through the cover sheet member 2 and provides a connection for secure attachment to an electrical return cable.

The webbing layer 3 has an inner surface 11 which contacts the person's body and an outer surface 10 which is secured at two spaced-apart points (generally at electrode ends 1A and 1B) to inner surface 9 of cover member by adhesive coatings designated by the numerals 12 and 13. In the preferred embodiment the adhesive coating 12 also serves to fix the end portion 5 of the conductive member 4 to the outer surface 10 of the webbing.

From the foregoing description it will be apparent that conductive member 4 is fixedly secured to both the cover sheet member 2 and the webbing layer 3 near one end of the body electrode 1, which end is generally designated by the numeral 1A. The opposite end of the body electrode 1 is generally designated by the numeral 1B. The edge 4B of conductive member 4 positioned near the end 1B of the electrode 1 as well as the major portion of the length of conductive member 4 (excepting only end portion 5) remain unsecured to both the inner surface 9 of the cover sheet member 2 and the outer surface 10 of the webbing layer 3.

Each end of the webbing layer 3 is provided with adhesive means preferably in the form of pressure sensitive adhesive coatings designated by the numerals 14A and 14B which are positioned at two spaced-apart points in the vicinity of electrode ends 1A, 1B on the inner surface 11 of the webbing layer 3. As will be seen, the two spaced-apart points span the unsecured portion of conductive member 4 (between secured end portion 5 and edge 4B), since this unsecured portion is disposed generally between adhesive coatings 14A and 14B.

Conventional "peel off" type covers 15A, 15B are provided to cover the adhesive coatings 14A and 14B while the electrode is in storage.

Figure 3:
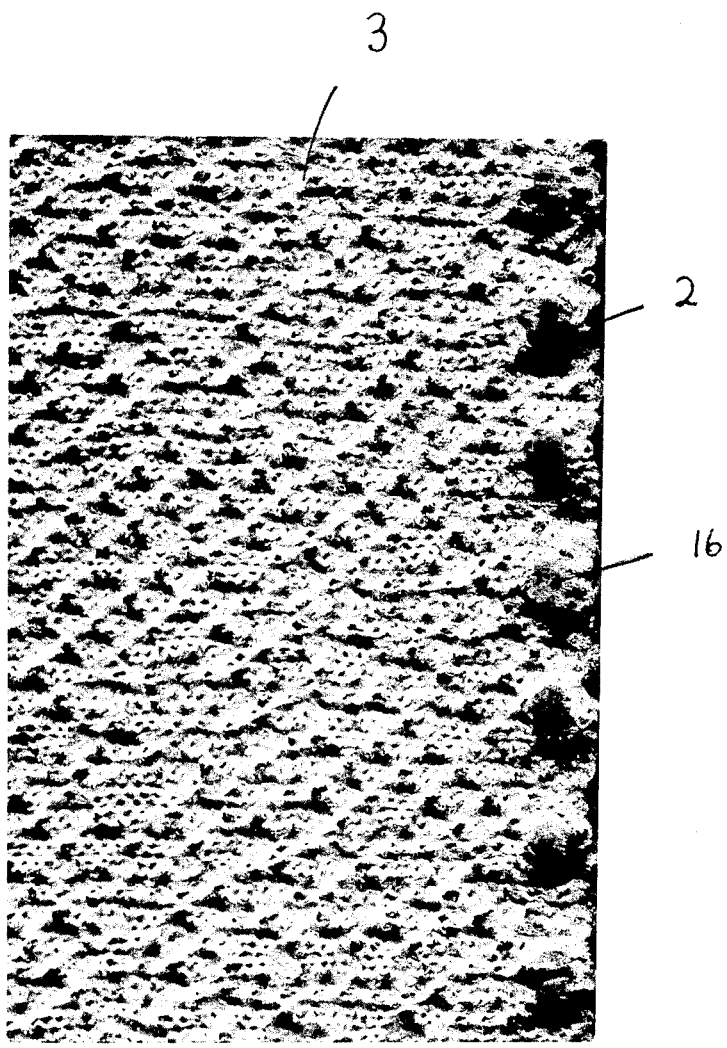
FIG. 3 is a detailed view in the form of an enlarged photograph, of the woven fibrous webbing of the embodiment of FIGS. 1 and 2, mounted on the foam rubber backing sheet.

As illustrated in FIG. 3, which is in fact a photograph enlarged approximately 4 times, of an edge portion of the webbing layer and attached elastic cover sheet, the webbing layer 3 is of interwoven single fibres, of polyester, specifically DACRON or FORTREL polyester fibre. The layer is approximately 1/16 inch thick and is porous, water permeable and hydrophobic. The nature of the fibre weave is such that the breaking of a fibre at a single location will not cause the webbing to split or rupture over any significant area of the webbing and thereby expose the metal plate 4 to contact with the skin. Specifically, the webbing layer in single knit, crepe stitch 100% polyester fibre fabric, the fibre having a denier of 150. The water permeability of the webbing is substantially the same at all locations across its area, so that the aqueous conductive medium applied evenly across its surface will penetrate evenly through to contact the metal plate 4. The webbing layer 3 is secured to the elastically stretchable cover sheet 2 by the series of ultrasound spot welds 16. The openness of the weave of the webbing layer 3 can be seen from the photograph comprising FIG. 3, wherein the dark areas are portions of the foam rubber cover sheet 2 showing through the webbing layer 3. The webbing layer as a whole is resiliently stretchable to an extent of about 100%.

The use and operation of the invention will now be described with reference to the foregoing detailed description. A liquid or semi-solid conductive medium of high (over 90%) water content is first spread over inner surface 11 of the webbing layer 3 on the area between adhesive coatings 14A and 14B. The conventional "peel off" covers 15A, 15B are then removed from coatings 14A and 14B. Because of the nature of the webbing previously described and the nature of the polyester fibres therein, the webbing layer does not absorb the conductive medium, but restrains its flow and holds it in place. It allows rapid penetration of the medium through to contact the surface of the metal plate 4, over the whole area to which the medium is initially applied.

The end 1A of the electrode is then attached to the body by means of the adhesive coating 14A. The opposite end 1B of the electrode is then forcibly gripped by the person applying electrode 1 and the electrode 1 (by reason of the stretchability of cover sheet member 2 and webbing plate 3) is then stretched over the patient's body (similar to the method of applying a bandaid to a body). The end 1B of electrode 1 is then secured to the body by means of the adhesive coating 14B. The conductive medium previously applied to and held by webbing layer 3 contacts and penetrates the patient's skin, to provide a good electrically conductive path from the body to the metal plate 4.

Elastic cover sheet member 2 has thus been stretched over flexible conductive sheet member 4. By reason of the elasticity of the former and the flexibility of the latter, cover sheet member 2 forces the unsecured portion of conductive sheet member 4 to flex into close conformity with the adjacent contours of the body. The unsecured portion of conductive sheet member 4 is thus forced (over its entire area) against webbing layer 3 holding the conductive medium, to achieve close and uniformly good electrical contact with the body.

As will be appreciated, the tensioned state of cover sheet member 2 tends to promote a firmer grip upon the body by adhesive coatings 14A, 14B because of the tension forces directly between them. As a result, the electrode shows excellent resistance to stresses applied at snap fastener 6 by an electrical return cable connected thereto.

It is to be understood that the particular embodiment of the invention described above and shown in the drawings is merely illustrative and not restrictive on the broad invention. It will be understood by those skilled in the art that various changes in design, structure and arrangement can be made without departing from the spirit of the broader aspects of the invention as defined in the appended claims.

What I claim is:

1. A body electrode useful as the return electrode in electro-surgical procedures, comprising: an elastically, resiliently stretchable cover sheet member having an inner surface for facing towards the body and an outer surface for facing away therefrom;

a flexible, electrically conductive metal sheet member connected to said cover sheet member having an outer surface presented towards the inner surface of said cover sheet member, and an inner surface for facing towards the body;

terminal means in electrically conductive relation to said metal sheet member;

means for attaching the body electrode to a patient's body;

a layer of water permeable woven fibrous webbing covering in its entirety the inner surface of said metal sheet member and extending beyond the peripheral edge thereof, and adapted to receive and restrain the flow of electrically conductive medium of thin semi-solid or fluid consistency applied thereto, said layer having a thickness of from about 1/50 to about ⅛ inch, the fibres of said webbing being of low water absorbency and being interwoven together into said webbing in interlocking fashion, said layer being secured to the cover sheet member at locations beyond the peripheral edge of said metal sheet member, and said layer being elastically resiliently stretchable along with the cover sheet member.

2. The body electrode of claim 1 wherein the conductive metal sheet member is attached to said cover sheet member near one end thereof, the remaining, major area portion of the conductive sheet member extending to the other end thereof remaining unsecured to the cover sheet member and thereby adapted to permit relative free movement between the cover sheet member and the conductive metal sheet member.

3. The body electrode of claim 2 wherein the fibrous webbing is elastically, resiliently stretchable in both the longitudinal and transverse directions to an extent of at least 20%.

4. The body electrode of claim 3 wherein the webbing layer is ultrasound welded to the elastic cover sheet member along opposed edges of the webbing layer at locations beyond the peripheral edges of the conductive metal sheet member.

5. The body electrode of claim 4 wherein the webbing is of a fibre selected from the group consisting of non-absorbent thermoplastic polyesters, non-absorbent thermoplastic polyamides, non-absorbent polyacrylonitriles, polyethylene and polypropylene.

6. The body electrode of claim 4 wherein the webbing is crepe polyester.

7. The body electrode of claim 4 wherein the webbing layer is adhesively secured to the elastic cover sheet member along opposed edges of the webbing layer other than said ultrasound welded opposed edges at locations beyond the peripheral edges of the conductive metal sheet member, the conductive metal sheet member being unsecured to and slidable with respect to the webbing layer.

8. In a body electrode for electro-medical use, including a cover sheet having an inner surface for facing towards a patient's body and an outer surface for facing away therefrom,
- a flexible, electrically-conductive panel having an outer surface presented towards the inner surface of said cover sheet, and an inner surface for facing towards the patient's body.
- a cover element superimposed on and overlying said conductive panel at the inner surface thereof,
- terminal means in electrically conductive relation to said conductive panel, and
- means for attaching the body electrode to the patient's body at a selectable zonal contact area thereof so as temporarily and removably to secure said electrode at the body contact area,
- means for attachment of said cover sheet to said cover element to sandwich and cone said electrically conductive panel therebetween whilst preserving shiftability of said conductive panel therebetween,
- the improvement wherein said cover element comprises web-like spacer means contiguous with said panel and functioning as an effective mechanical barrier interface to preclude objectionable direct physical contact between said conductive panel and a patient's body during securement of said electrode to the body, and wherein said means for attachment of said cover sheet to said cover element includes first adhesive means permanently bonding said spacer means at opposed ends thereof to said cover sheet, and bonding means permanently securing said spacer means to said cover sheet along overlying coextensive lateral edges thereof, whereby said spacer means, at a principal body-contacting zone thereof, is unsecured to and is freely slidable with respect to both said cover sheet and said electrically-conductive panel, and
- wherein said means for attaching the body electrode to the patient's body comprises second adhesive means coating opposed end portions of said spacer means,
- said spacer means consisting essentially of a crepe, resiliently stretchable, foraminous, interwoven non-conductive sheet coextensive with and covering the entire areal expanse of the inner surface of said conductive panel, and
- wherein said spacer means is porous and fluid-permeable, being adapted to permit interpenetration into and passage of an electrically-conductive, mobile, fluid-like medium through interstices extending transversely through said spacer means while restricting lateral flow and dispersion of the medium from the zonal contact area cover by said conductive panel;
- thereby to ensure functional retention of the electrically conductive medium as a thin conductive layer of essentially uniform thickness between said conductive panel and the patient's body to maintain electrical contact therebetween, and to promote even current distribution over the zonal contact area,
- said web-like spacer means having a thickness of from about 1/50 to about ⅛ inch and being further characterized by low water absorbency.

* * * * *